(12) United States Patent  
Gündel et al.

(10) Patent No.: US 7,751,605 B2
(45) Date of Patent: Jul. 6, 2010

(54) METHOD AND DEVICE FOR VISUALIZING A SEQUENCE OF TOMOGRAPHIC IMAGE DATA RECORDS

(75) Inventors: Lutz Gündel, Erlangen (DE); Matthias Thorn, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 876 days.

(21) Appl. No.: 11/636,451

(22) Filed: Dec. 11, 2006

(65) Prior Publication Data

US 2007/0230761 A1   Oct. 4, 2007

(30) Foreign Application Priority Data

Dec. 12, 2005   (DE)   ........................ 10 2005 059 209

(51) Int. Cl.
*G06K 9/00* (2006.01)
(52) U.S. Cl. ........................ 382/128; 382/130; 382/131; 382/294
(58) Field of Classification Search ................. 382/128, 382/130, 131, 294
See application file for complete search history.

(56) References Cited

U.S. PATENT DOCUMENTS

| 5,526,812 | A | 6/1996 | Dumoulin et al. | |
|---|---|---|---|---|
| 6,771,262 | B2 | 8/2004 | Krishnan | |
| 7,158,692 | B2 * | 1/2007 | Chalana et al. | ............. 382/294 |
| 7,186,991 | B2 * | 3/2007 | Kato et al. | ............... 250/492.1 |
| 2003/0174872 | A1 | 9/2003 | Chalana et al. | |
| 2005/0185829 | A1 * | 8/2005 | Heismann | .................. 382/128 |
| 2005/0277830 | A1 * | 12/2005 | Ichihara | ...................... 600/425 |
| 2006/0052702 | A1 * | 3/2006 | Matsumura et al. | ......... 600/443 |

FOREIGN PATENT DOCUMENTS

| DE | 195 42 605 A1 | 5/1996 |
|---|---|---|
| DE | 199 55 690 A1 | 6/2000 |
| DE | 103 40 544 A1 | 3/2005 |
| DE | 103 40 546 A1 | 3/2005 |

OTHER PUBLICATIONS

German Office Action dated Sep. 26, 2006.

* cited by examiner

*Primary Examiner*—Tom Y Lu
(74) *Attorney, Agent, or Firm*—Harness, Dickey & Pierce, P.L.C.

(57) ABSTRACT

A method and a device are disclosed for visualizing a sequence of tomographic image data records of an examination volume that has been recorded at a time interval from one another. In at least one embodiment of the method, the image data records are firstly registered with one another. On the basis of the registration with regard to a display perspective and a displayed volume region identical views are generated from at least three of the image data records and displayed on an imaging surface of a graphic display unit in a fashion superposed on one another with adjustable weighting and/or adjustable transparency. For the superposed display, there are inserted on the imaging surface one or more controllers by whose interactive operation an operator can adjust or vary the weighting and/or transparency with which the at least three views are superposed. The present method and the associated device, in at least one embodiment, allow an operator to evaluate the corresponding image data records with a reduced outlay on time.

19 Claims, 3 Drawing Sheets

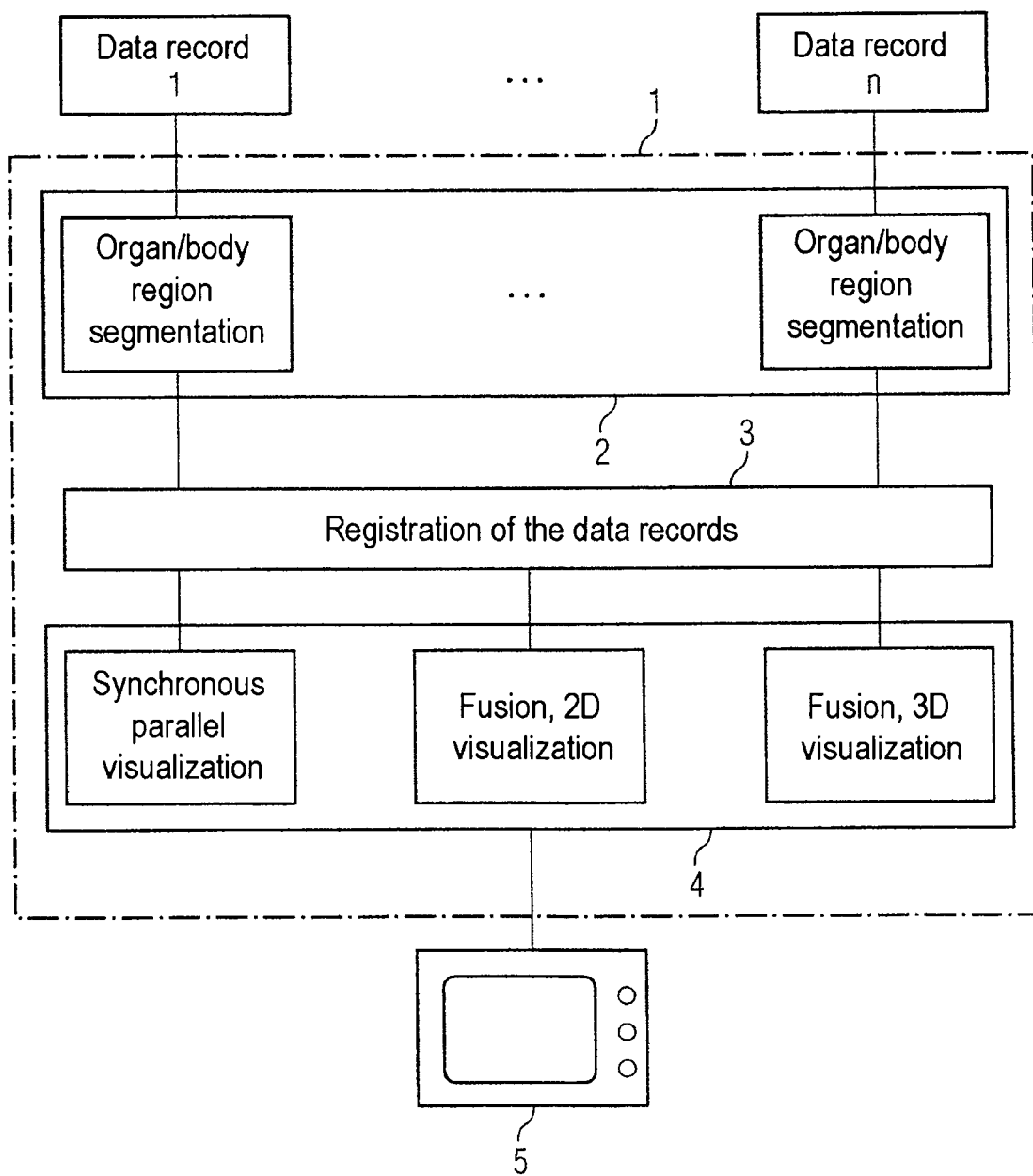

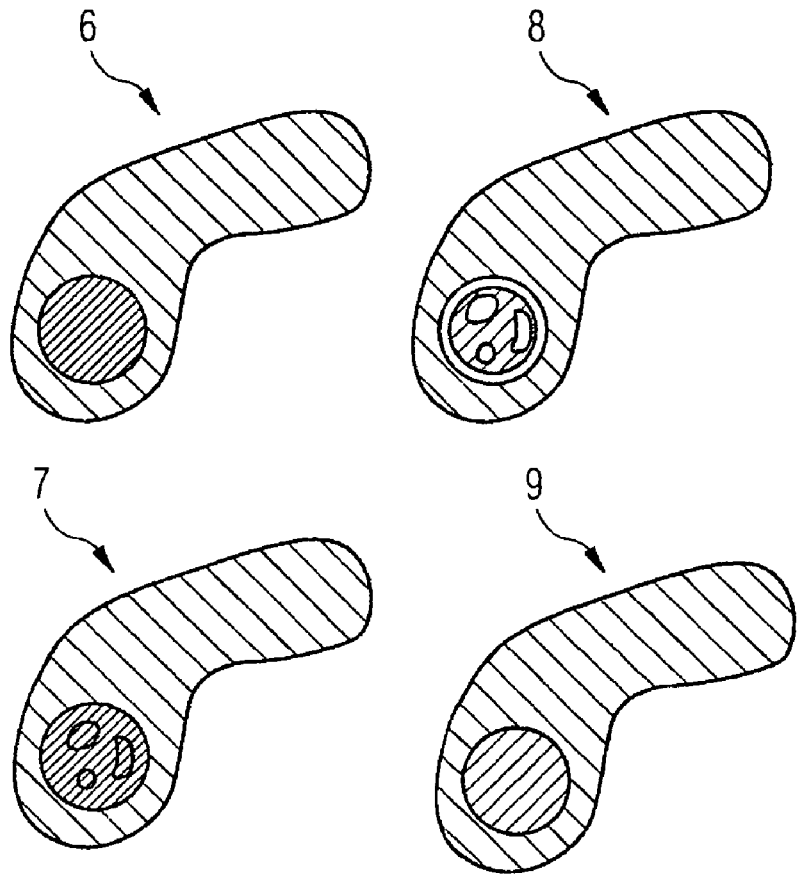
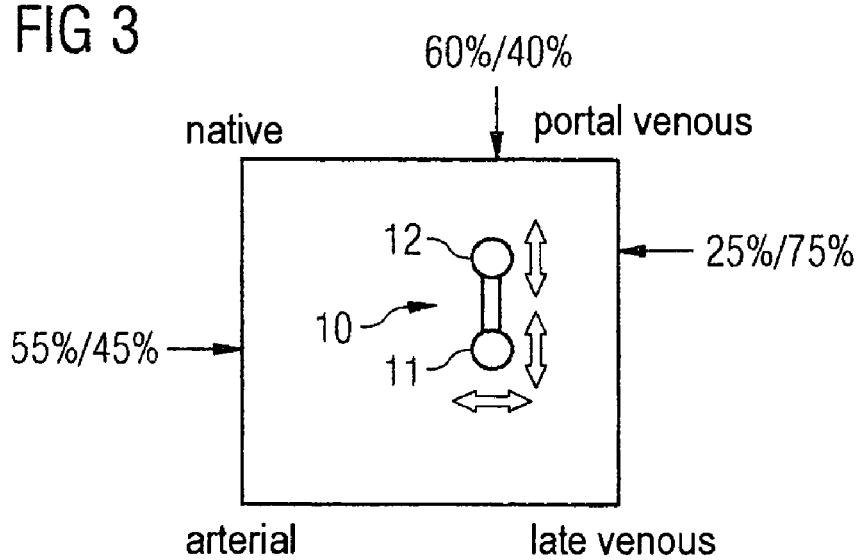

METHOD AND DEVICE FOR VISUALIZING A SEQUENCE OF TOMOGRAPHIC IMAGE DATA RECORDS

PRIORITY STATEMENT

The present application hereby claims priority under 35 U.S.C. §119 on German patent application number DE 10 2005 059 209.0 filed Dec. 12, 2005, the entire contents of which is hereby incorporated herein by reference.

FIELD

Embodiments of the present invention generally relate to a method and/or a device for visualizing a sequence of tomographic image data records of an examination volume that have been recorded at a time interval from one another.

BACKGROUND

Sequences of tomographic image data records are chiefly recorded and visualized in medical imaging. Thus, for example, in order to detect tumors in the liver, a number of computed tomography (CT) scans are generally carried out firstly without and subsequently with intravenous administration of contrast agent. Depending on the type of tumor examined, the contrast agent becomes enriched at a different strength at different times and with a different distribution in the tumor and/or in the tissue surrounding it.

In addition to the images of the CT scan without contrast agent, use is made for the purpose of detecting a tumor of the so-called native scan, three further tomographic image data records that have been recorded at different points in time after contrast agent administration. Here, in liver diagnosis measuring times are selected that have an optimum contrast of the arteries, of the portal venous vessel system including the liver parenchyma and the outflow of the contrast agent from the liver parenchyma. At most four image data records are searched for lesions during the finding. If a lesion is found in a data record, the corresponding positions in the other data records are analyzed and the diagnosis is derived therefrom.

Different tumor types can also frequently be concerned, and so it may be necessary to conduct the search in more than four data records that have been recorded at different measuring times during the contrast agent administration. Since the tomographic image data records are volume data records or 3D image data records, searching the individual image data records has so far been a time consuming method for the user.

SUMMARY

In at least one embodiment of the present invention, a method and a device are specified for visualizing a sequence of tomographic image data records of an examination volume that enables the doctor to evaluate the image data records in a shorter time.

During the method of at least one embodiment, for visualizing a sequence of tomographic image data records of an examination volume that have been recorded at a time interval from one another, the image data records are firstly registered with one another. The person skilled in the art is aware of suitable algorithms for registering tomographic image data records. This can involve both a rigid registration and a non-rigid registration of the image data records in the case of which consideration is given to a movement of the examination volume or objects comprised therein, in particular a movement or deformation of an organ, for example of the heart, lung or intestine.

The first step for the registration is preferably to segment the body regions and/or organs to be examined in the image data records. This can be performed, for example, by manually setting landmarks or else by means of automatic image processing tools. If algorithms that permit the registration of the complete image data records are used for the registration, the upstream segmentation step for the registration can be omitted.

In at least one embodiment of the present method, on the basis of the registration with regard to the display perspective and the displayed volume region identical views are then generated from at least three of the image data records and displayed on an imaging surface of a graphic display unit in a fashion superposed on one another with adjustable weighting and/or adjustable transparency. For the superposed display of the views there are inserted on the imaging surface one or more controllers by way of whose interactive operation, in particular by way of whose displacement, an operator can adjust or vary the individual weighting and/or transparency of the superposed views.

The one or more controllers can preferably be displaced in more than two directions over a region bounded on the imaging surface, the individual views being assigned to different edge segments of the region. The image data records can be evaluated in a particularly advantageous way for the operator by way of this possibility of intervention. The operator thereby sees the equivalent views from the respective image data records in a superposed fashion such that he need no longer change between these views during evaluation. However, the operator is displayed the identical or equivalent view, for example the display of a slice in the axial section, or a VRT (Volume Rendering Technique) display, in a simultaneous fashion from the participating image data records.

Here, the images can be the originally reconstructed axial images, but also coronal, axial, sagital or arbitrarily aligned secondary reconstructions, for example multiplanar reconstructions (MPR).

The method and the associated device enable the operator advantageously to navigate interactively in at least one of the image data records, or to vary his view interactively. In this case, the display of the other image data records is correspondingly corrected automatically in synchronous fashion in order respectively to show views corresponding with regard to the display perspective and the displayed volume region.

The method and the device of at least one embodiment are suitable here, in particular, for applications such as were explained in the introductory part of the present description. These are chiefly applications in which three or more image data records must be evaluated in order to examine the existence of a lesion or a tumor. The present method and the associated device are therefore designed for superimposing at least three views from three different image data records, preferably four such views or image data records.

The method and the device of at least one embodiment are also suitable for tumor aftercare. In the case of this aftercare, aftercare examinations are carried out at time intervals of weeks or months in order to detect a variation in tumor size, that is to say tumor growth or tumor reduction as success in the therapy. In this case, it is necessary respectively to compare 1-4 current image data records with a further 1-4 image data records recorded at an earlier time. This can also be performed with the aid of at least one embodiment of the present method and at least one embodiment of the present device through suitable superposition of the earlier image data records with the current image data records. The superposition adjustments can likewise be varied here with the aid of the controllers. However, it should additionally be possible to decouple the controllers, that is to say it should be possible to operate them independently of one another.

The device includes a data processing unit and a graphic display unit, the data processing unit having a registration module and a visualization module, in order to carry out the registration and visualization in accordance with the present method.

BRIEF DESCRIPTION OF THE DRAWINGS

The present method is explained in more detail once more below with the aid of an example embodiment in conjunction with the drawings, without restricting the scope of protection prescribed by the patent claims. In the drawings:

FIG. 1 shows an example of the schematic method sequence in the case of an example embodiment of the present method;

FIG. 2 shows an example of four views of a liver tumor;

FIG. 3 shows an example of an interactively inserted controller unit for adjusting the different weighting in the case of the superposed display of the views;

DETAILED DESCRIPTION OF THE EXAMPLE EMBODIMENTS

Figure 4:
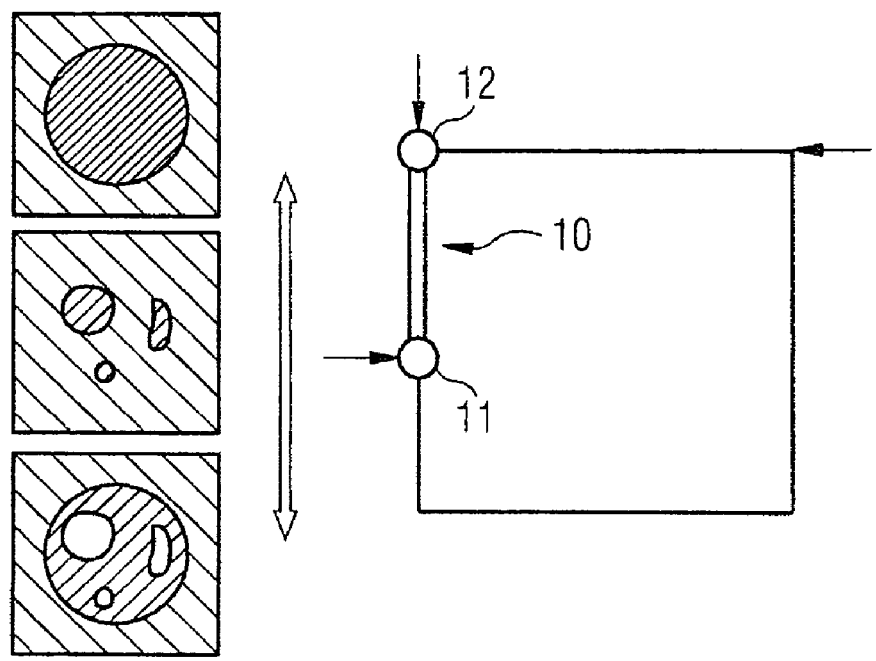
FIG. 4 shows an example of the display for a specific adjustment of the controller unit of FIG. 3.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

An embodiment of the present method is briefly explained once more with the aid of a method sequence illustrated by way of example in FIG. 1. Provided here firstly are the different image data records 1 . . . n, for example CT image data records of a volume scan. These image data records are further processed in the data processing unit 1 in the present device. In this example, an organ/body region segmentation is firstly performed in the segmentation module 2 in order to segment the organs and/or body regions for the later evaluation of the image data records. On the basis of this segmentation, the registration module 3 then carries out a registration of the image data records that is required for the later generation of equivalent views from the image data records. Finally, on the basis of this segmentation the corresponding simultaneous display of the equivalent views is generated in the visualization module 4 from the different image data records. This can be a synchronous parallel visualization, a superposed 2D visualization after a 2D image fusion, or else a superposed 3D visualization after a 3D image fusion. The display is performed on the monitor 5 indicated in the figure, which is connected to the visualization module 4.

FIG. 2 shows an example of four views of a liver tumor (hepatocellular carcinoma) in greatly simplified form. It is possible here to display simultaneously as tomogram views on the monitor the four views from four different image data records that are identical to the display perspective and the displayed volume region. To be seen in the view of the native scan 6 is a sharply bounded, hypodense mass owing to the reduced CT value (indicated in the figure by denser hatching). To be seen in the view of the arterial phase 7 are hyperdense areas (indicated in the figure by hatching that is less dense), which are distinguished by a higher CT value. A capsule is then to be seen owing to a bright edge in the view of the portal venous phase 8. The tumor contrast is reduced in the last view of the late venous phase 9. Other tumor types can effect a different increase or decrease in the CT values at other times.

An improved possibility of evaluation results when the individual views superposed on one another in accordance with an embodiment of the present method with the aid of weighting that can be adjusted or varied by the operator are displayed. In this example, the two-dimensional segments respectively of interest from tomograms of the image data records are fused for this purpose, and the fusion result is displayed on the screen. The first step here is respectively to fuse two views with adjustable weighting, after which the two resulting (fused) views are superposed, in turn, with a selectable weighting. To this end, there is inserted for the operator a controller unit 10 having two controller buttons 11 and 12, which in this example are coupled with regard to a horizontal displacement.

The individual views of the four image data records are assigned to the corners of the rectangle illustrated in FIG. 3. In the fused graphic display, the native scan and the scan of the arterial phase are superposed at a ratio of 55%:45%. This ratio can be varied by moving the controller button 11 upward and downward. The image data records of the portal venous and the late venous phases are mixed in the ratio of 25%:75% with the aid of the other controller button 12, likewise by upward and downward movement. The overall superposition (60%:40%) is adjusted by moving the controller unit 10 to the right/left from the two controller buttons 11, 12 coupled in this displacement direction.

Figure 5:
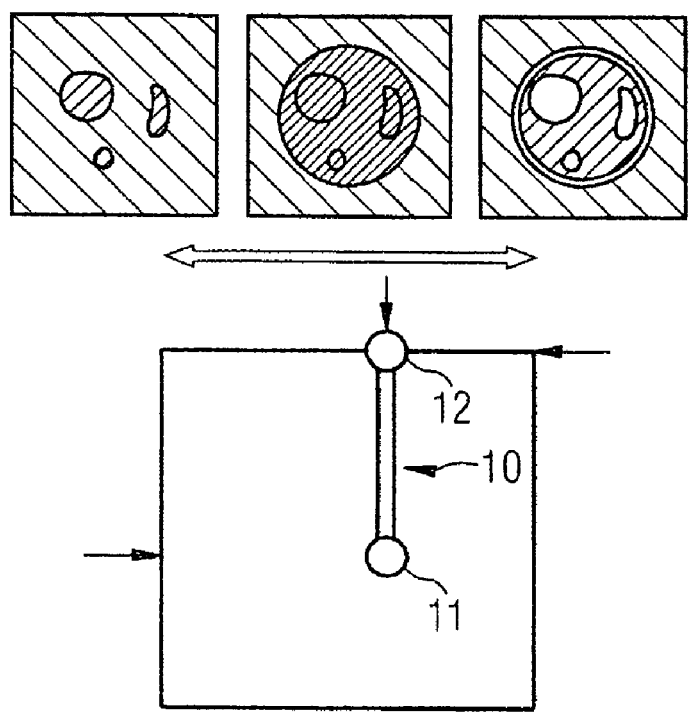
FIG. 5 shows an example of the display for another adjustment of the controller unit in accordance with FIG. 3.

FIGS. 4 and 5 show a possible mode of procedure for evaluating the image data records with reference to the example of the hepatocellular carcinoma. The first step in determining the extent of the tumor is simply to use a view of the native scan 6 and of the scan of the arterial phase 7. The controller unit 10 is therefore pushed at this instant up to the left-hand edge. By varying the controller button 11 in a vertical direction (FIG. 4) and subsequently varying the entire controller unit 10 in a horizontal direction (FIG. 5), the maximum extent of the tumor is then determined. The views corresponding to the different positions of the controller in FIG. 4 are to be seen in the left-hand part of this figure.

The late venous phase does not provide additional information in this simplified consideration, and so use is made only of the portal venous phase in the further consideration. To this end, FIG. 5 illustrates, in turn, three views that correspond to different positions of the controller. The horizontal displacement of the controller unit 10 thereby inserts the capsule of the tumor.

The examples illustrated in the figures show the superposed display of two-dimensional views. In a further refinement, it is also possible to use a display that conveys a three-dimensional image impression, also denoted as 3D visualization. Here, the tumor can be displayed, for example, by means of a volume rendering technique. The views of the individual phases and/or image data records are then likewise superposed by means of fusion. The technique used in the case of the two-dimensional display, and the controller described there can be used for this superposition.

In addition to the use of different weighting, the superposition of the individual views can also be performed with the aid of different coloration and/or adjustable transparency.

If the detail of interest, for example the tumor, cannot be detected in one of the views and therefore cannot be segmented, it therefore cannot be displayed. This can be shown to the operator by setting the controller automatically into one of the extreme positions.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing a sequence of tomographic image data records of an examination volume which has been recorded at a time interval from one another, comprising:
   registering the image data records; and
   generating, on the basis of the registration with regard to a display perspective and a displayed volume region, identical views from at least three image data records and displaying them on an imaging surface of a graphic display unit in a fashion superposed on one another with at least one of adjustable weighting and adjustable transparency, wherein for the superposed display, one or more controllers are inserted on the imaging surface by way of whose interactive operation, the at least one of weighting and transparency of the at least three views are at least one of adjustable and variable by an operator.

2. The method as claimed in claim 1, wherein, in order to superpose four views, a rectangle is at least one of inserted and used, in which a first and a second controller element are located, each corner of the rectangle being assigned one of the views, the weighting of the superposition of the first two views that are assigned to the corners of a first side of the rectangle being adjusted by displacing the first controller element parallel to this side, the weighting of the superposition of the second two views assigned to the corners of a second side of the rectangle opposite the first one being adjusted by displacing the second controller element parallel to the first side, and the weighting of the superposition of the second views on the first ones being adjusted by displacing the two controller elements perpendicular to the first side, the two controller elements being rigidly coupled to one another for this displacement.

3. The method as claimed in claim 1, wherein, in order to superpose four views, a first (11), a second and a third controller element are inserted, the weighting of the superposition of a first and a second of the four views being adjusted, in order to form a first superposed view, by moving the first controller element, the weighting of the superposition of a third and a fourth of the four views being adjusted, in order to form a second superposed view, by moving the second controller element, and the weighting of the superposition of the first and the second superposed view being adjusted by moving the third controller element.

4. The method as claimed in claim 1, wherein at least one region of interest is segmented from the image data records, and wherein the registration is performed on the basis of the segmented regions.

5. The method as claimed in claim 1, wherein the image data records are 3D image data records of computed tomography pictures, and wherein at least one of 2D view 3D view is selectable with the aid of which the image data records are displayed.

6. The method as claimed in claim 1, wherein, in at least one of the image data records, an operator is enabled to at least one of navigate and vary the view, the display of the other image data records then being correspondingly corrected automatically in synchronous fashion.

7. The method as claimed in claim 1, wherein views of image data records, that differ from one another in examination volume, are displayed.

8. A device for visualizing a sequence of tomographic image data records of an examination volume that have been recorded at a time interval from one another, comprising:
   a data processing unit including a registration module, to register the image data records, and a visualization module to generate identical views from at least three of the image data records on the basis of the registration with regard to a display perspective and the displayed volume region; and
   a graphic display unit to display, on an imaging surface, the identical views from at least three of the image data records in a fashion superposed on one another with at least one of adjustable weighting and adjustable transparency, wherein the visualization module is designed such that for the superposed display, there is inserted on the imaging surface, at least one controller, by whose interactive operation the at least one of weighting and transparency of the at least three views is at least one of adjustable and variable by an operator.

9. The device as claimed in claim 8, wherein, in order to superpose four views, the visualization module inserts a first and a second controller element in at least one of a rectangle and on an imaging surface forming a rectangle, each corner of the rectangle being assigned one of the views, the weighting of the superposition of the first two views assigned to the corners of a first side of the rectangle is adjustable by displacing the first controller element parallel to this side, the weighting of the superposition of the second two views assigned to the corners of a second side of the rectangle being adjustable opposite the first one by displacing the second controller element parallel to the first side, the weighting of the superposition of the second views on the first ones are adjustable by displacing the two controller elements perpendicular to the first side, and the two controller elements being rigidly coupled to one another for this displacement.

10. The device as claimed in claim 8, wherein, in order to superpose four views, the visualization module inserts a first, a second and a third controller element, the weighting of the superposition of a first and a second of the four views is adjustable, in order to form a first superposed view, by moving the first controller element, the weighting of the superposition of a third and a fourth of the four views being adjustable, in order to form a second superposed view, by moving the second controller element, and the weighting of the superposition of the second superposed view on the first one is adjustable by moving the third controller element.

11. The device as claimed in claim 8, wherein the data processing unit comprises a segmentation module by which at least one region of interest is segmented from the image data records, the registration module carrying out the registration on the basis of the segmented regions.

12. The device as claimed in claim 8, wherein the visualization module is designed such that it enables an operator at least one of, navigate in at least one of the image data records, and vary the view from this image data record, and wherein it then correspondingly corrects the display of the other image data records automatically in a synchronous fashion.

13. The method as claimed in claim 2, wherein at least one region of interest is segmented from the image data records, and wherein the registration is performed on the basis of the segmented regions.

14. The method as claimed in claim 3, wherein at least one region of interest is segmented from the image data records, and wherein the registration is performed on the basis of the segmented regions.

15. The device as claimed in claim 9, wherein the data processing unit comprises a segmentation module by which at least one region of interest is segmented from the image data records, the registration module carrying out the registration on the basis of the segmented regions.

16. The device as claimed in claim 10, wherein the data processing unit comprises a segmentation module by which at least one region of interest is segmented from the image data records, the registration module carrying out the registration on the basis of the segmented regions.

17. The device as claimed in claim 9, wherein the visualization module is designed such that it enables an operator at least one of, navigate in at least one of the image data records, and vary the view from this image data record, and wherein it then correspondingly corrects the display of the other image data records automatically in a synchronous fashion.

18. The device as claimed in claim 10, wherein the visualization module is designed such that it enables an operator at least one of, navigate in at least one of the image data records, and vary the view from this image data record, and wherein it then correspondingly corrects the display of the other image data records automatically in a synchronous fashion.

19. The device as claimed in claim 11, wherein the visualization module is designed such that it enables an operator at least one of, navigate in at least one of the image data records, and vary the view from this image data record, and wherein it then correspondingly corrects the display of the other image data records automatically in a synchronous fashion.

* * * * *